United States Patent [19]

Holstedt et al.

[11] Patent Number: 4,533,480

[45] Date of Patent: Aug. 6, 1985

[54] BIS(HYDROCARBYLOXY METHYLATED) BORON-CONTAINING, HETEROCYCLIC COMPOUNDS AND LUBRICATING COMPOSITIONS CONTAINING THE SAME

[75] Inventors: Richard A. Holstedt, Whittier; Peter J. Jessup, Santa Ana, both of Calif.

[73] Assignee: Union Oil Company of California, Los Angeles, Calif.

[21] Appl. No.: 476,513

[22] Filed: Mar. 18, 1983

[51] Int. Cl.$^3$ .................. C10M 1/20; C10M 1/32; C10M 1/54

[52] U.S. Cl. .................. 252/46.4; 252/47.5; 252/49.6; 252/49.7; 260/462 R; 556/7; 534/15

[58] Field of Search .................. 252/46.4, 47.5, 49.6, 252/49.7; 260/429.7, 429.9, 435 R, 438.1, 260/439 R, 462 R, 429.5, 438.5 R, 429 R

[56] References Cited

U.S. PATENT DOCUMENTS

| | | | |
|---|---|---|---|
| 2,441,063 | 5/1948 | Gilmann | 260/404 |
| 3,011,880 | 12/1961 | Liao et al. | 44/63 |
| 3,224,971 | 12/1965 | Knowles et al. | 252/46.3 |
| 3,227,739 | 1/1966 | Versteeg | 260/462 R |
| 3,256,310 | 6/1966 | Weil | 260/462 |
| 3,269,853 | 8/1966 | English et al. | 106/243 |
| 3,598,855 | 8/1971 | Cyba | 260/462 R |
| 3,642,652 | 2/1972 | Birgy | 252/389 |
| 4,136,039 | 1/1979 | Jager et al. | 252/8.8 |
| 4,176,076 | 11/1979 | Waldstein | 252/49.6 |
| 4,204,972 | 5/1980 | Knoblauch et al. | 252/78.1 |
| 4,226,734 | 10/1980 | Schuster | 252/49.3 |
| 4,382,006 | 5/1983 | Horodysky | 252/49.6 |

OTHER PUBLICATIONS

U.S. Application No. 91,903, filed Nov. 6, 1979 to Horodysky.

*Primary Examiner*—W. J. Shine
*Attorney, Agent, or Firm*—Dean Sandford; Gregory F. Wirzbicki; Cleveland R. Williams

[57] ABSTRACT

Certain bis(hydrocarbyloxy methylated) boron-containing, heterocyclic compounds are disclosed which impart extreme pressure, anti-wear and friction reducing properties to lubricating oils. Such oils may be further provided with a hydrocarbon polysulfide derivative of 2,5-dimercapto-1,3,4-thiodiazole as a copper corrosion inhibitor, or terephthalic acid as a lead corrosion inhibitor, or either a bis(dithiobenzil)metal derivative or a sulfur bridged, bis hindered phenol as an oxidation inhibitor, or mixtures thereof.

34 Claims, No Drawings

BIS(HYDROCARBYLOXY METHYLATED) BORON-CONTAINING, HETEROCYCLIC COMPOUNDS AND LUBRICATING COMPOSITIONS CONTAINING THE SAME

BACKGROUND OF THE INVENTION

1. Field of the Invention

This invention relates to lubricating oils and more particularly to improved lubricating oils containing additives, such as corrosion inhibitors, oxidation inhibitors and extreme pressure, anti-wear and friction reducing compounds.

2. Description of the Prior Art

It is well recognized in the petroleum industry that boron containing compounds are desirable additives for lubricating oils. One such boron containing compound is disclosed in U.S. Pat. No. 3,224,971 to Knowles et al. which relates to intracomplexed borate esters and to lubricating compositions containing said esters. The borate esters are organo-boron compounds derived from boric acid and a bis (o-hydroxy-alkylphenyl) amine or sulfide. These compounds are described as additives for lubricating oils.

Boric-acid-alkylolamine reaction products and lubricating oils containing the same are disclosed in U.S. Pat. No. 3,227,739 to Versteeg. These amine type products are prepared by reacting equal molar proportions of diethanolamine or dipropanolamine and a long chain, 1,2-epoxide. The intermediate reaction product thus produced is reacted with boric acid to produce the final reaction product. These compounds are added to lubricants to prevent rust formation.

As can readily be determined from the above, there is an ongoing effort to develop lubricating compositions having improved properties.

Accordingly, it is an object of the present invention to provide a boron-containing, oxygenated heterocyclic compound or metal derivative thereof which has extreme pressure, anti-wear and friction reducing properties.

Yet another object of the present invention is to provide a lubricating composition having extreme pressure, anti-wear and friction reducing properties.

A further object of the present invention is to provide a lubricating composition containing extreme pressure, anti-wear, friction reducing and corrosion prevention additives, and in addition, an anti-oxidant to prevent attack of oxidants upon metal bearings.

Other objects and advantages of the invention will be apparent from the following description.

SUMMARY OF THE INVENTION

In one embodiment of the present invention, there are provided certain bis(hydrocarbyloxy methylated), boron-containing heterocyclic compounds wherein the hydrocarbyloxy methyl groups are of the formulas —$CH_2$—O—R, where R is a substituted or unsubstituted organic radical containing carbon and hydrogen atoms, with the number of carbon atoms usually being between 1 and 50. Compounds of the present invention have the following chemical formula:

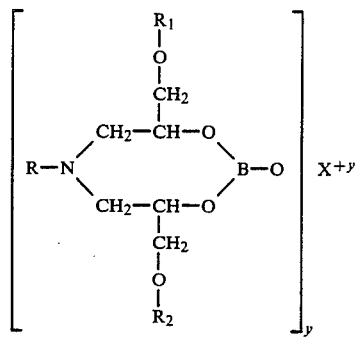

where R is hydrogen or an organic radical having from 1 to about 30 carbon atoms, $R_1$ and $R_2$ are the same or different organic radicals having from 1 to about 50 carbon atoms, y is an integer between 1 and 4, and X is hydrogen or a metal selected from a transition metal having an atomic number of 21 through 30 or a Group IVA metal.

The foregoing compounds may be prepared generally by reacting ammonia or a primary amine having 1 to 30 carbon atoms with a glycidyl ether having 4 to 53 carbon atoms. Next, the amine thus produced is reacted with boric acid to produce a bis(hydrocarbyloxy methylated), boron-containing heterocyclic compound. The metal derivative of these heterocyclic compounds may be produced by reacting said heterocyclic compound with a transition metal having an atomic number of 21 through 30 or a Group IVA metal.

Another embodiment of the invention resides in a lubricating composition comprising bis(hydrocarbyloxy methylated), boron-containing heterocyclic compounds of the invention or metal derivatives thereof, said lubricant composition being further provided on an optional basis with any of (1) a polysulfide derivative of 2,5-dimercapto-1,3,4-thiadiazole, (2) terephthalic acid, and (3) either a bis(dithiobenzil) metal derivative or a sulfur bridged, bis hindered phenol or a mixture thereof.

The above-described bis(hydrocarbyloxy methylated), boron-containing heterocyclic compounds of the invention impart extreme pressure, anti-wear and friction reducing, properties to lubricating oils when added to said oils at use concentrations.

DETAILED DESCRIPTION OF THE INVENTION

The present invention resides in bis(hydrocarbyloxy methylated), boron-containing, heterocyclic compounds and a method of preparing the same, and lubricating compositions containing the same.

Boron-containing heterocyclic compounds suitable for use herein have the following formula:

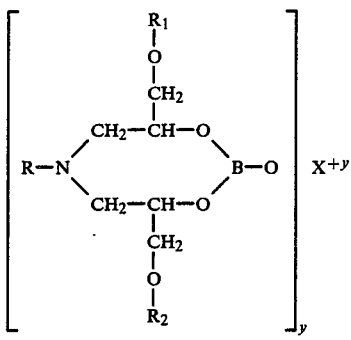

where R is hydrogen or an organic radical having from 1 to about 30 carbon atoms. Preferably, R is hydrogen or alkyl, alkene, alkadiene, aryl, alkylaryl or arylalkyl. Generally, $R_1$ and $R_2$ are the same or different organic radicals having from 1 to about 50 carbon atoms, y is an integer between 1 and 4, and X is hydrogen or a metal selected from a transition metal having an atomic number of 21 through 30 or a Group IVA metal as disclosed in the Periodic Table located in the Handbook of Chemistry and Physics, 46th Edition.

When R, $R_1$ and $R_2$ are organic radicals, usually at least 65 percent, more usually at least 75 percent, and most usually at least 90 percent of the atoms composing said radicals will be carbon and hydrogen atoms. Preferably, R is hydrogen or an alkyl, alkene, alkadiene, aryl, alkylaryl, or arylalkyl radical having from 1 to about 30 carbon atoms, and more preferably, from 1 to about 24 carbon atoms. On the other hand, $R_1$ and $R_2$ are preferably the same or different radicals selected from alkyl, aryl, alkylaryl and arylalkyl radicals having from 1 to about 50 carbon atoms, and more preferably from 1 to about 30 carbon atoms, and more preferably still from 1 to about 20 carbon atoms, and most preferably from 1 to about 10 carbon atoms.

Another embodiment of the present invention resides in lubricating compositions having extreme pressure, anti-wear, friction reducing, corrosion inhibition and anti-oxidant properties which comprise a major amount of a lubricating oil and a minor amount of a bis(hydrocarbyloxy methylated) boron-containing, heterocyclic compound or a metal derivative of said compound. Optionally, these lubricating compositions may contain any of (1) a hydrocarbon polysulfide derivative of 2,5-dimercapto-1,3,4-thiadiazole, (2) terephthalic acid, and (3) a bis(dithiobenzil) metal derivative, or a sulfur bridged, bis hindered phenol or a mixture thereof.

Primary amines useful in preparing the bis(hydrocarbyloxy methylated), boron-containing, heterocyclic compounds [herein denominated bis(hydrocarbyloxy methylated) boramid compounds] and metal derivatives of this invention may be produced by reacting ammonia with organic halides, such as the alkyl, aryl, alkylaryl or arylalkyl halides having 1 to 30 carbon atoms, using conventional techniques and apparatus. These halides react with ammonia at moderately high temperatures and under pressure to produce a mixture of primary, secondary and tertiary amines. The primary amine yield of this process may be improved by using an excess of ammonia in the reaction.

Another typical process for producing primary amines consists of reacting alcohols with ammonia in the vapor phase at a temperature of from 570° F. to 940° F. and a pressure from 200 to 1,000 p.s.i.g. For the lower molecular weight alcohols, temperatures of 750° F., pressures of about 200 p.s.i.g. and a reaction time of 2 to 3 hours are desirable. The alcohols and ammonia may be conveniently obtained from commercial sources. A mixture of primary, secondary and tertiary amines is formed wherein the amines exist in equilibrium with each other. It is possible to improve the yield of the desired amine by recycling undesired amines through the vapor phase. These primary amines are, in addition, commercially available.

Saturated or unsaturated primary amines are conventionally prepared by reacting an unsaturated fatty acid with ammonia to produce an ammonium soap. The ammonium soap is heated to produce an amide. The amide thus produced is heated in the presence of a standard dehydration catalyst to produce a nitrile. The nitrile is contacted with hydrogen gas at increased temperature to produce either an unsaturated amine or a saturated amine depending upon the degree of hydrogenation the nitrile is subjected to.

Primary amines useful in preparing the bis(hydrocarbyloxy methylated) boramid compounds of the present invention have the chemical formula $RNH_2$ wherein R is hydrogen or an organic radical, preferably where R contains no more than 30 carbon atoms for example, from 1 to 24 carbon atoms. Among the suitable amines are methyl amine, ethylamine, propylamine, butylamine, octadecyl amine, cyclohexylamine, dodecylamine, phenylamine, oleylamine, cocoamine and tallowamine and mixtures thereof.

In preparing the bis(hydrocarbyloxy methylated) boramid compounds, these primary amines are typically reacted with an alkyl, aryl alkylaryl or arylalkyl glycidyl ether to produce a bis(hydrocarbyloxy methylated) primary amine. Glycidyl ethers suitable for use herein preferably have the formula:

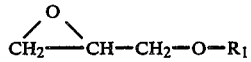

where $R_1$ is an organic radical having 1 to 50 carbon atoms, said organic radical in a preferred mode comprises at least 75 percent, preferably 90 percent of carbon and hydrogen atoms, preferably $R_1$ is an alkyl, aryl, alkylaryl or arylalkyl radical having from 1 to about 50 carbon atoms, preferably from 1 to about 30 carbon atoms, more preferably still from 1 to about 20 carbon atoms, and most preferably from 1 to about 10 carbon atoms.

A wide variety of glycidyl ethers may be used to prepare the oxylated primary amines needed to produce the boramid compounds herein. Typical glycidyl ethers for use herein include methyl glycidyl ether, ethyl glycidyl ether, propyl glycidyl ether, butyl glycidyl ether, phenyl glycidyl ether, cresyl glycidyl ether, phenyl methyl glycidyl ether, ethyl phenyl glycidyl ether and phenyl ethyl glycidyl ether and mixtures thereof.

The primary amine is normally reacted with the glycidyl ether in the presence of a solvent, for example, toluene, methanol or water to produce a dioxygenated amine. The solvent is added in sufficient quantity to dissolve or disperse the reactants to insure better contact thereof.

Generally the primary amine and glycidyl ether are reacted at a pressure of from about atmospheric pressure to about 500 p.s.i.g. at a temperature of from 176°

F. to 450° F., for 1 to 30 hours. The primary amine is preferably reacted with the glycidyl ether at a molar ratio of 1:2 to produce the bis(hydrocarbyloxy methylated) amine. It may be desirable to react the primary amine with two different glycidyl ethers to produce a mixed hydrocarbyloxy methylated amine. In this embodiment of the invention, one mole of the primary amine is reacted with one mole each of two different glycidyl ethers to produce the desired mixed hydrocarbyloxy methylated amine. Yet another method of producing the desired amine involves reacting one mole of an aromatic glycidyl ether and one mole of an alkyl glycidyl ether with a primary amine to produce an amine having an aromatic moiety and an alkyl moiety attached to the nitrogen atom of the primary amine.

Next, the bis(hydrocarbyloxy methylated) amine or mixed hydrocarbyloxy methylated amine is reacted with boric acid at a molar ratio of from about 1:2 to about 1:1 in the presence of a solvent, for example, xylene, benzene, toluene, or the like, to produce a bis(-hydrocarbyloxy methylated) boron-containing, heterocyclic compound of the present invention, i.e., a bis(hydrocarbyloxy methylated)boramid compound. Normally, the solvent will comprise from about 20 to about 50 weight percent, preferably from about 30 to about 40 weight percent of the reaction mixture. The reaction is conducted under reflux at a temperature of from 176° F. to 450° F., preferably from 176° F. to 300° F., at a pressure of from atmospheric pressure to about 500 p.s.i.g. for about 1 to about 30 hours. The compound thus produced will contain from about 0.5 to about 10 weight percent, preferably from about 2 to about 5 weight percent of boron.

In a preferred mode the primary amine and glycidyl ether are first reacted together and the intermediate reaction product thus produced is, next, reacted with boric acid.

An alternative method of producing the bis(hydrocarbyloxy methylated) boron-containing, heterocyclic compounds herein involves reacting the primary amine, glycidyl ether and boric acid in a one-step process.

Representative bis(hydrocarbyloxy methylated), boron-containing, heterocyclic compounds produced in accordance with the procedure herein include the following compounds: 1-hydroxy-3,7-di(methoxy methyl)-5-dodecyl-5-aza-1-bora-2,8-dioxacyclooctane; 1-hydroxy-4,6-di(methoxy methyl)-5-dodecyl-5-aza-1-bora-2,8-dioxacyclooctane; 1-hydroxy-3,7-di(ethoxy methyl)-5-dodecyl-5-aza-1-bora-2,8-dioxacyclooctane; 1-hydroxy-3,7-di(propoxy methyl)-5-dodecyl-5-aza-1-bora-2,8-dioxacyclooctane; 1-hydroxy-4,6-di(butoxy methyl)-5-dodecyl-5-aza-1-bora-2,8-dioxacyclooctane; 1-hydroxy-3,7-di(methyl phenoxy methyl)-5-dodecyl-5-aza-1-bora-2,8-dioxacyclooctane; 1-hydroxy-4,6-di(-methyl phenoxy methyl)-5-dodecyl-5-aza-1-bora-2,8-dioxacyclooctane; 1-hydroxy-3,7-di(ethyl phenoxy methyl)-5-dodecyl-5-aza-1-bora-2,8-dioxacyclooctane; 1-hydroxy-4,6-di(phenyl methoxy methyl)-5-dodecyl-5-aza-1-bora-2,8-dioxacyclooctane; and 1-hydroxy-3,7-di(phenyl ethoxy methyl)-5-dodecyl-5-aza-1-bora-2,8-dioxacyclooctane and mixtures thereof. It should be noted that the methyl, ethyl, propyl, butyl, cyclohexyl, octadecyl, phenyl, stearyl, oleyl, coco and tallow moieties may be substituted for the dodecyl moiety in the above heterocyclic compounds.

Metal derivatives of the bis(hydrocarbyloxy methylated), boron-containing, heterocyclic compounds, herein are conveniently prepared by contating the compound with a metal, usually in soft form. Thus, the metal acetates, propionates, etc., are suitable for use. The preferred metal compound for use in incorporating the metal ion into the boramid compound is the metal acetate. Generally, these compounds are reacted with the metal compounds in a molar ratio range of from about 1:4 to about 6:1, preferably from about 1:1 to about 4:1, at a pressure of from about atmospheric to about 500 p.s.i.g. and a temperature of from about 176° F. to about 450° F.

Desirable metals are usually selected from transition metals having an atomic number of 21 through 30 or Group IVA metals of the Periodic Table. Transition metals which are suitable for use are selected from scandium, titanium, vanadium, chromium, manganese, iron, cobalt, nickel, copper and zinc and mixtures thereof. Suitable Group IVA metals include lead and tin and mixtures thereof. Normally, the metal will comprise from about 1 to about 17 weight percent, preferably from about 5 to about 9 weight percent of the compound. When a metal is incorporated into the compounds herein, the metal will displace and substitute for the hydrogen atom attached to the oxygen atom which is a component of the hydroxy group attached to the boron atom of the boramid structure.

Representative of the metal compounds are: copper di[-1-oxy-2,7-di(methoxy methyl)-5-dodecyl-5-aza-1-bora-2,8-dioxacyclooctane]; copper di[-1-oxy-4,6-di(-methoxy methyl)-5-dodecyl-5-aza-1-bora-2,8-dioxacyclooctane]; copper di[-1-oxy-3,7-di(ethoxy methyl)-5-dodecyl-5-aza-1-bora-2,8-dioxacyclooctane]; copper di[-1-oxy-3,7-di(propoxy methyl)-5-dodecyl-5-aza-1-bora-2,8-dioxacyclooctane]; copper di[-1-oxy-4,6-di(-butoxy methyl)-5-dodecyl-5-aza-1-bora-2,8-dioxacyclooctane]; copper di[-1-oxy-3,7-di(methyl phenoxy methyl)-5-dodecyl-5-aza-1-bora-2,8-dioxacyclooctane]; copper di[-1-oxy-4,6-di(methyl phenoxy methyl)-5-dodecyl-5-aza-1-bora-2,8-dioxacyclooctane]; copper di[-1-oxy-3,7-di(ethyl phenoxy methyl)-5-dodecyl-5-aza-1-bora-2,8-dioxacyclooctane]; copper di[-1-oxy-4,6-di(phenyl methoxy methyl)-5-dodecyl-5-aza-1-bora-2,8-dioxacyclooctane]; and copper di[-1-oxy-3,7-di(phenyl ethoxy methyl)-5-dodecyl-5-aza-1-bora-2,8-dioxacyclooctane and mixtures thereof. Other metals which may be incorporated into the above compounds, i.e., substituted for the copper, include scandium, titanium, vanadium, chromium, manganese, iron, cobalt, nickel, zinc, lead and tin and mixtures thereof. In addition, methyl, ethyl, propyl, butyl, cyclohexyl, octadecyl, phenyl, steryl, oleyl, coco and tallow moieties may be substituted for the dodecyl moiety in the above-described compounds.

Normally, the bis(hydrocarbyloxy methylated), boron-containing, heterocyclic compounds herein or metal derivatives thereof are blended with a lubricating oil at a concentration of from 0.1 to about 15 weight percent, preferably from 0.5 to about 10 weight percent of the oil composition.

Use of copper and lead in the construction of improved internal combustion engines has created problems in the use of extreme pressure additives in lubricants for such engines, the primary problem being the leaching out of copper and lead from bearings used in said engines.

Copper corrosion in engine bearings is inhibited by adding to the lubrication composition a corrosion inhibiting amount, normally from 0.001 to about 5 weight percent, preferably from 0.005 to about 2.5 weight percent of a hydrocarbon polysulfide derivative of 2,5-dimercapto-1,3,4-thiadiazole having the formula:

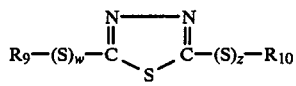

wherein $R_9$ and $R_{10}$ are the same or different moieties selected from hydrogen or straight or branched chain alkyl, cyclic or alicyclic alkyl, aryl, alkylaryl or arylalkyl radicals having from 2 to about 30 carbon atoms, and w and z are integers between 1 and 8. It should be noted that $R_9$ and $R_{10}$ cannot both be hydrogen because the compound would be rendered insoluble in lubricating oils. Thus, when $R_9$ is hydrogen, $R_{10}$ must be selected from one of the other moieties described above, and vice versa.

The herein-described polysulfide derivatives of 2,5-dimercapto-1,3,4-thiadiazole can be suitably prepared by several methods. For example, they can be prepared by reacting 2,5-dimercapto-1,3,4-thiadiazole with a suitable sulfenyl chloride, or by reacting the dimercaptan with chlorine and reacting the resultant disulfenyl chloride below,

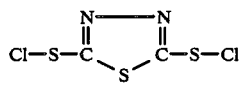

with a primary or tertiary mercaptan. Bis-trisulfide derivatives are obtained by reacting the dimercaptan with a mercaptan and a sulfur chloride in molar ratios of from 1:2:2 to 1:2:4 at a temperature of from about 120° to 212° F. Higher polysulfides may be prepared by reacting the thiadiazole di or trisulfides with sulfur at temperatures of about 200° F. to 400° F. Another method of preparing the polysulfides of the present invention involves reacting 2,5-dimercapto-1,3,4-thiadiazole with a mercaptan and sulfur in the molar ratio of from 1:1:1 to 1:4:16 at temperatures of from about 160° F. to about 300° F. The 2-mercapto, 5 alkyldithio-1,3,4-thiadiazole derivative may be prepared by reacting less than the stoichiometric amount of a primary or tertiary mercaptan with the disulfenyl chloride above to produce the bis form of the compound.

Compounds produced in accordance with the above procedure preferably are polysulfides of 1,3,4-thiadiazole-2,5-bis(alkyl, di, tri or tetra sulfide) containing from 2 to about 30 carbon atoms. Desirable polysulfides include 1,3,4-thiadiazole-2,5-bis (octyldisulfide); 1,3,4-thiadiazole-2,5 bis(octytrisulfide); 1,3,4-thiadiazole-2,5 bis (octyltetrasulfide); 1,3,4-thiadiazole-2,5 bis (dodecyldisulfide); 1,3,4-thiadiazole-2,5 bis (dodecyltrisulfide); 1,3,4-thiadiazole-2,5 bis (dodecyltetrasulfide); 2-lauryldithia-5-thiaalphamethylstyryl-1,3,4 thiadiazole; 2-lauryltrithia-5-thiaalphamethylstyryl-1,3,4 thiadiazole; 2-mercapto-5-octyldithio-1,3,4-thiadiazole and 2-mercapto-5-dodecyldithio-1,3,4-thiadiazole and mixtures thereof.

An especially desirable ratio of the above copper corrosion inhibitors, when two are mixed together, is from 1:20 to 20:1, preferably from 1:10 to 10:1.

A small but effective amount of terephthalic acid is the preferred lead corrosion inhibitor herein. The terephthalic acid may be prepared in accordance with conventional techniques and apparatus. For example, para-xylene may be oxidized to terephthalic acid at elevated temperature and pressure in the presence of acetic acid, a bromine promoter and a heavy metal catalyst, i.e., cobalt, manganese, etc. A second method of preparing terephthalic acid comprises reacting benzene and potassium carbonate over a cadmium catalyst at increased temperature and pressure. Generally, the terephthalic acid is incorporated into lubricating oils at a concentration of from about 0.001 to about 1 weight percent, especially from about 0.01 to about 0.05 weight percent.

The oxidation inhibitors or anti-oxidants herein have high enough molecular weights to ensure that they remain stable in a hot crankcase oil, e.g. 300° F. and, in addition, enhance the corrosion preventive properties of the copper and lead corrosion inhibitors by interrupting or terminating the attack of oxidants upon copper/lead-bearing metal. One type of corrosion is an oxidative process involving the loss of electrons from the corroding metal by an oxidant such as oxygen, air, nitrogen oxides, partially burned gasoline, blow-by products and the like. The oxidation inhibitors as describe hereinafter are selected from the group consisting of bis(dithiobenzil) metal derivatives and sulfur bridged, bis hindered phenols and mixtures thereof. These compounds effectively limit or prevent the attack of oxidants on copper/lead metal. In addition, these compounds also help to control oil oxidation as manifested by reduced sludge and varnish formation, and by reduced oil thickening.

The bis(dithiobenzil) metal derivatives herein preferably have the formula:

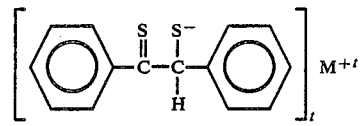

wherein M is a first row transition metal and t is an integer between 1 and 4. Suitable transition metals include vanadium, chromium, manganese, iron, cobalt, nickel, copper, zinc, preferably iron, cobalt and nickel.

Generally, the bis(dithiobenzil) metal derivatives are prepared in accordance with conventional techniques and procedures. For example, benzoin is reacted with phosphorus sulfide in the presence of dioxane at elevated temperature to produce the thiophosphoric ester of dithiobenzoin. The desired divalent metal, for example, metallic halide, is reacted with the above-described thiphosphoric ester of dithiobenzoin to produce the bis(dithiobenzil) metal derivative.

It should be noted that the bis(dithiobenzil) metal derivatives herein do not readily dissolve in lubricant compositions. However, when the bis(dithiobenzil) metal derivatives are mixed with the boramid compounds herein, especially dodecylamino di(phenylethylate) hydrogen borate, the mixtures goes into solution in lubricant compositions such as motor oils. Although the invention is not bound by any theory, it is believed that the bis(hydrocarbyloxy methylated) boramid compound and bis(dithiobenzil) metal derivative form a complex which renders the bis(dithiobenzil) metal derivative soluble in lubricants, for example, motor oil.

The sulfur bridged, bis hindered phenols herein preferably have the formula:

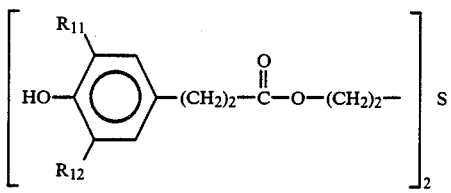

wherein $R_{11}$ and $R_{12}$ are selected from the same or different alkyl groups having from 1 to 6 carbon atoms.

In general, the sulfur bridged, bis hindered phenols are prepared by conventional esterification procedures using a suitable alcohol and an acid of the formula:

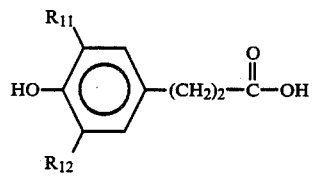

or an an acid halide, acid anhydride or mixed anhydride thereof, and wherein $R_{11}$ and $R_{12}$ are as described before. The suitable alcohol herein preferably is thiodiglycol having the formula $(HOCH_2CH_2)_2S$ which is prepared by the hydrolysis of dichloroethyl sulfide or the interaction of ethylene chlorohydrin and sodium sulfide using conventional techniques and procedures.

Sulfur bridged, bis hindered phenols which are suitable for use as anti-oxidants include thiodiethyl bis-(3,5-dimethyl-4-hydroxy)hydrocinnamate; thiodiethyl bis-(3,5-diethyl-4-hydroxy)hydrocinnamate; thiodiethyl bis-(3,5-dipropyl-4-hydroxy)hydrocinnamate; thiodiethyl bis-(3,5-dibutyl-4-hydroxy)hydrocinnamate; thiodiethyl bis-(3,5-dipentyl-4-hydroxy)hydrocinnamate and mixtures thereof.

Generally, the anti-oxidants herein are incorporated into lubricant compositions at concentrations of from 0.01 to about 1 weight percent, preferably from 0.025 to about 0.10 weight percent.

The extreme pressure, anti-wear, friction reducing corrosion inhibition and anti-oxidation additives described herein may be incorporated in a wide variety of lubricating oils, for example, mineral oil, (including automobile engine oil), synthetic oil, industrial oils, for example, cutting oil, metal working fluids and grease. In addition, the additives may be added to lubricating oils derived from paraffins, naphthenic or mixed base crude petroleum oils, that have been subjected to solvent and/or sulfuric-acid treatment, aluminum chloride treatment, hydrogenation and/or other refining treatments. In addition, the additives described herein may be incorporated in petroleum distillates, such as diesel fuel, jet engine fuel, furnace oil, gas oil and other light oils.

Preferred distillate lubrication oils which are improved by the addition of the additives herein have an initial boiling point within the range of 350° F. to about 475° F., an end point in the range of about 500° F. to about 1,100° F., and a flash point not lower than 110° F.

Lubricants derived from oil shale are particularly desirable for use herein. Oil shale is a form of compact sedimentary rock, generally laminated, that contains little or no oil but does contain organic material, usually known as kerogen, derived from aquatic organisms or waxy spores and pollen grains, which is convertible to oil by heat. Crude shale oil, in combination with water, gas and spent shale containing a carbonaceous residue and mineral matter, is formed by the pyrolysis of oil shale. The hydrocarbons of shale oil are highly unsaturated, resembling the products of thermal cracking of petroleum, as would be expected because of the pyrolytic origin of shale oil. Once the shale oil is extracted, it is subjected to conventional hydrotreating procedures to produce a variety of hydrocarbon products, including lubricants.

Synthetic lubricating oils useful herein are those oils derived from a product of chemical synthesis (man-made oils). Typical examples of such compositions include the polyglycol fluids (i.e., polyalkylene glycol); silicones which consist of a silicone-oxygen polymer chain to which are attached hydrocarbon branches composed of either alkyl or phenyl groups; phosphates; polyphenyl esters; synthetic hydrocarbons and various esters of organic acids and alcohols.

The polyalkylene glycol lubricating oils suitable for use herein preferably are derived from the reaction product of the appropriate alkylene oxides. The alkylene moiety of the above compositions have a carbon chain of from about 1 to about 10 carbon atoms, preferably from about 2 to about 7 carbon atoms and a molecular weight within the range of from about 200 to 2,000, preferably from about 200 to about 1,000, most preferably from about 200 to about 800. Representative examples of suitable polyalkylene glycols include, polyethylene glycol, polypropylene glycol, polyisopropylene glycol, polybutylene glycol and the like.

Synthetic lubricating oils derived from hydrocarbons are generally of two types, namely, dialkylated benzene and polymerized alpha-olefins. Dialkylated benzene herein is formed from the condensation product of the appropriate alkyl compound and has a carbon chain from about 5 to about 50 carbon atoms, preferably from about 8 to about 20 carbon atoms; and a molecular weight of from about 200 to about 1,500, preferably from about 300 to about 700. Representative compounds include di-n-decylbenzene, n-decyl-n-tetradecylbenzene, and n-nonyl-n-dodecylbenzene.

Alpha-olefins suitable for use in preparing lubricating oils herein are characterized by the formula $RCH=CH_2$ wherein R is a radical selected from the group of hydrogen and alkyl radicals having from about 4 to about 18 carbon atoms, preferably from about 6 to about 10 carbon atoms, and having a molecular weight of from about 80 to about 300, preferably from about 100 to about 200. Typical compounds include 1-octene, 1-decene and 1-dodecene.

Phosphates suitable for use herein as synthetic lubricating oils are the phosphate esters having the formula $O=P(OR)_3$, wherein R is aryl or alkyl having from about 4 to about 20 carbon atoms, preferably from 6 to about 10 carbon atoms, and have a molecular weight within the range of from about 200 to about 1,000, preferably from about 300 to about 550. Representative compounds include trioctyl phosphate, tricresyl phosphate and dicresyl methyl phosphate.

Esters of organic acids which are suitable for use herein as synthetic lubricating oils preferably are selected from organic acids having carbon chains of from $C_4$ to $C_{40}$ carbon units. Organic acids which may be reacted with the alcohols herein include caproic, decanoic, sebacic, laurel, oleic, stearic, palmitic, etc. Likewise, alcohols herein derived from either natural or synthetic origin, for example, pentaerythritol, trimethylolpropane, amyl, 2-ethyl-hexanol or laurel alcohol, may be used to form the desired ester. The esters are formed using conventional methods. For example, the esters may be prepared by reaction of the desired alcohol with the desired acid, acid anhydride or acid halide using conventional reaction conditions and techniques.

If desired, the additives described herein may be employed in conjunction with other additives commonly used in petroleum products. Thus, there may be added to the oil compositions of this invention rust inhibitors, emulsifying agents, dyes, haze inhibitors, anti-static agents, detergents, dispersants, viscosity index improvement agents, pour point reducing agents, other extreme pressure additives, corrosion inhibitors and oxidation inhibitors. Soaps or other thickening agents may be added to the lubricating oil compositions to form compositions having the consistency of a grease. When other additives are employed, it may be desirable, although not necessary to prepare additive concentrates comprising concentrated solutions of the herein boron or metal-boron derivatives together with said other additives whereby the several additives are added simultaneously. Dissolution of the additive or additive concentrate into the oil composition may be facilitated by mixing accompanied with mild heating, but this is not absolutely essential.

The invention will be further described with reference to the following examples.

EXAMPLE I

The bis(hydrocarbyloxy methylated)boramid compound, 1-hydroxy-3,7-di(methyl phenoxy methyl)-5-coco-5-aza-1-bora-2,8-dioxacyclooctane, is prepared by adding 278.5 grams of cocoamine[1] and 450.5 grams of cresyl glycidyl ether to a 2-liter round-bottomed flask that contains 250 ml of toluene and 22 ml of water. The flask is placed in a heating mantle and fitted with a water-cooled condenser. The mixture thus formed is heated until it begins to reflux. Next, the temperature is adjusted to give a moderate reflux rate and the reaction mixture is refluxed for 18 hours. The reaction mixture is cooled to room temperature and 86.0 grams of boric acid are added to the flask. Then, the flask is placed in a heating mantle and fitted with a water-cooled condenser. The mixture thus formed is heated until it begins to reflux. Next, the temperature is adjusted to give a moderate reflux rate and the reaction mixture is refluxed for 18 hours. The reaction mixture is cooled to room temperature and 86.0 grams of boric acid are added to the flask. Then, the flask is equipped with a Dean-Stark trap topped with a water-cooled condenser and the reaction mixture is refluxed until water stops collecting in the trap. Toluene is distilled from the reaction product at a temperature of 400° F. The reaction produces 748.5 grams of 1-hydroxy 3,7-di(methyl phenoxy methyl)-5-coco-5-aza-1-bora-2,8-dioxacyclooctane.

(1) Cocoamine is a mixture of primary amines consisting of approximately 52 percent dodecylamine, 19 percent of tetradecylamine, 9 percent of hexadecyl amine, 6.5 percent of octylamine, 6 percent of decylamine, 2 percent of octadecyl amine and 5 percent of a mixture of octadecenylamine and octadecadienylamine. Cocoamine is produced commercially by the Armak Company under the tradename of Armeen CD.

EXAMPLE II

The bis(hydrocarbyloxy methylated)boramid compound, 1-hydroxy-3,7-di(methyl phenoxy methyl)-5-oleyl-5-aza-1-bora-2,8-dioxacyclooctane, is prepared by adding 55.6 grams of oleyl amine and 66.0 grams of cresyl glycidyl ether to a 1-liter round-bottomed flask that contains 250 ml of toluene. The flask is placed in a heating mantle and fitted with a water-cooled condenser. The mixture thus formed is heated until it begins to reflux. Next, the temperature is adjusted to give a moderate reflux rate and the reaction mixture is refluxed for 18 hours. The reaction mixture is cooled to room temperature and 12.4 grams of boric acid are added to the flask. Then, the flask is equipped with a Dean-Stark trap topped with a water-cooled condenser and the reaction mixture is refluxed until water stops collecting in the trap. Toluene is distilled from the reaction product at a temperature of 400° F. The reaction produces 97 grams of 1-hydroxy-3,7-di(methyl phenoxy methyl)-5-oleyl-5-aza-1-bora-2,8-dioxacyclooctane.

EXAMPLE III

The bis(hydrocarbyloxy methylated)boramid compound, 1-hydroxy-3,7-di(methyl phenoxy methyl)-5-dodecyl-5-aza-1-bora-2,8-dioxacyclooctane, is prepared in accordance with the procedure of Example I with the following exception: one mole of dodecyl amine is substituted for each mole of cocoamine used.

EXAMPLE IV

The bis(hydrocarbyloxy methylated)boramid compound, 1-hydroxy-3,7-di(methyl phenoxy methyl)-5-tallow-5-aza-1-bora-2,8-dioxacyclooctane, is prepared in accordance with the procedure of Example II with the following exception: one mole of tallowamine[2] is substituted for the oleyl amine.

(2) Tallowamine is a mixture of amines consisting of approximately 29 percent hexadecylamine, 20.5 percent octadecylamine, 44 percent of a mixture of octadecenylamine and octadecadienylamine, 3 percent tetradecylamine, 1.5 percent hexadecenylamine, 1 percent heptadecylamine and 0.5 percent tetradecenylamine. Tallowamine is marketed commercially by the Armak Company under the trademark Armeen T.

EXAMPLE V

A copper derivative of 1-hydroxy-3,7-di(methyl phenoxy methyl)-5-coco-5-aza-1-bora-2,8-dioxacyclooctane is prepared by following the procedure of Example I with the following exception: the above described compound (47 grams), 100 ml of toluene, 20 ml of triethyl amine and 10 grams of cupric acetate are mixed in a single-necked, 500 ml round bottom flask, equipped with a heating mantle, Dean-Stark trap and water-cooled condenser. The mixture is refluxed for 16 hours, then filtered and the toluene, amine, water and acetic acid (produced in situ) are distilled from the reaction product. Using the above procedure, copper di[1-oxy-3,7-di(methyl phenoxy methyl)-5-dodecyl-5-aza-1-bora-2,8-dioxacyclooctane] is produced.

EXAMPLE VI

Lead di[-1-oxy-3,7-di(methyl phenoxy methyl)-5-coco-5-aza-1-bora-2,8-dioxacyclooctane] is prepared by following the procedure of Example I with the following exception:

The reaction product produced in Example I (23.5 grams), 100 ml of toluene, 9.5 grams of lead acetate and 100 ml of triethylamine are mixed in a single-necked 500 ml round bottom flask, equipped with a water-cooled condenser and heating mantle and Dean-Stark trap. The mantle heat is adjusted until a moderate rate of reflux is obtained. The mixture thus formed is refluxed for 18 hours. Next, the mixture is filtered, toluene, water, triethylamine and acetic acid (produced in the reaction) are distilled from the reaction product.

EXAMPLE VII

Iron di[-1-oxy-3,7-di(methyl phenoxy methyl)-5-tallow-5-aza-1-bora-2,8-dioxacyclooctane] is prepared according to the procedure of Example IV with the following exception:

A mixture comprising 23.5 grams of the reaction product produced in Example IV, 100 ml of toluene, 4.3 grams of ferrous acetate and 100 ml of triethylamine are introduced into a single-necked 500 ml round-bottom flask, equipped with Dean-Stark trap, water cooled condenser and heating mantle. The heating mantle is adjusted to give a moderate rate of reflux of the reaction mixture. The mixture is refluxed for 18 hours. Next, the mixture is filtered and the triethylamine, toluene, and acetic acid (produced in the reaction) are distilled from the reaction product.

EXAMPLE VIII

A nickel derivative of 1-hydroxy-3,7-di(methyl phenoxy methyl)-5-oleyl-5-aza-1-bora-2,8-dioxacyclooctane is prepared by following the procedure of Example II with the following exceptions:

A mixture comprising 23.5 grams of the reaction product produced in Example II, 100 ml of toluene, 10 grams of nickel acetate and 100 ml of triethylamine are mixed in a single-necked 500 ml round-bottom flask, equipped with a water-cooled condenser and heating mantle and Dean-Stark trap. The mantle heat is adjusted until a moderate rate of reflux is obtained. The mixture thus formed is refluxed for 18 hours. Next, the mixture is filtered and toluene, water, triethylamine and acetic acid (produced in the reaction) are distilled from the reaction product. The reaction produces nickel di[-1-oxy-3,7-di(methyl phenoxy methyl)-5-oleyl-5-aza-1-bora-2,8-dioxacyclooctane].

EXAMPLE IX

The copper corrosion inhibitor, 1,3,4-thiadiazole-2,5-bis(dodecyldisulfide), is prepared by chlorinating 284 grams of n-dodecyl mercaptan in 0.6 liter of carbon tetrachloride with 1.47 moles of chlorine over a two hour period at a temperature of about 23° F. to about 32° F. Next, sulfenyl chloride which forms as a reaction product is stripped with nitrogen to remove hydrogen chloride, and the resultant compound is added to 86 grams of a 2,5-dimercapto-1,3,4-thiadiazole slurry. The mixture is heated at 86° F. for 1½ hours and the resultant compound (1,3,4-thiadiazole-2,5-bis(dodecyldisulfide) is recovered by washing with water and sodium bicarbonate and vacuum stripping to remove carbon tetrachloride.

EXAMPLE X

The procedure of Example XXIX is followed to prepare 1,3,4-thiadiazole-2,5-bis(octyldisulfide) with the following exception: octyl mercaptan is substituted for the dodecylmercaptan.

EXAMPLE XI

The oxidation inhibitor, bis(dithiobenzil)iron (II) is prepared by adding 400 grams of benzoin and 600 grams of phosphorus sulfide to a single-necked 5 liter, round bottom flask equipped with heating mantle and water-cooled condenser and containing 1,500 ml of dioxane. The mixture thus formed is refluxed for two hours. Next, 200 grams of hydrated ferrous chloride dissolved in 500 ml of water is added to the 5 liter flask and the mixture is heated on a steam bath (212° F.) for 2 hours. The reaction product thus formed (169.5 grams) is filtered and washed with methanol.

EXAMPLE XII

The oxidation inhibitor, bis(dithiobenzil)nickel, is prepared by adding a mixture of 100 grams of benzoin, 150 grams of phosphorus sulfide and 700 ml of dioxane to a 5 liter, single necked flask equipped with heating mantle and water cooled condenser. The above-described mixture is, then, refluxed for 2 hours, during which the thiophosphoric ester of dithiobenzoin is formed and hydrogen sulfide is evolved. The reaction mixture is cooled and a solution of 50 grams of nickel chloride (hydrated) in 200 ml of water is added to the flask and heated (212° F.) for 2 hours on a steam bath. Black crystals of bis(dithiobenzil)nickel are formed and collected by filtering the cooled solution. Purification is effected by extraction with boiling toluene.

It should be noted that other bis(dithiobenzil) metal derivatives may be prepared in accordance with the above procedures by substituting transition metals or Group IVA metals as described herein for the nickel described above.

EXAMPLE XIII

The oxidation inhibitor, thiodiethyl bis-(3,5-di-t-butyl-4-hydroxy)hydrocinnamate, is prepared by melting together 17.95 weight percent of B,B'-dihydroxy-diethyl sulfide, 81.41 weight percent of (3,5-di-t-butyl-4-hydroxy)hydrocinnamate acid and 0.64 weight percent of sodium methylate under a nitrogen atmosphere at 266° F. for two and one-half hours. Methanol thus formed is separated from the reaction mixture and condensed in a dry-ice bath using nitrogen gas as a carrier. The reactants are heated at 149° F. for three hours and the reaction product is dissolved in warm benzene, filtered and the benzene filtrate is washed three times with saturated sodium chloride solution. The filtrate is, next, dried over anhydrous sodium sulfate and the solvent evaporated using convention techniques. Thiodiethyl bis-(3,5-di-t-butyl-4-hydroxy)hydrocinnamate is isolated and purified by successive recrystallization from hexane and a mixture of hexane and t-butanol.

EXAMPLE XIV

A lubricant composition is tested for friction reducing properties and copper and lead corrosion inhibition properties using a single-cylinder Labeco CLR Test Engine equipped with sintered copper (65 wt. %)/lead (35 wt. %) connecting rod bearings, in accordance with the procedure of Federal Test Method Standard No. 791B, Method 3405.2. The lubricant composition used is a standard 450 neutral oil containing the additives and concentrations disclosed in Table 2 below.

The test is conducted in accordance with the test conditions of Table 1 below:

TABLE 1

| Operating Conditions | |
|---|---|
| Test Duration, Hours | 40 |
| Speed, RPM | 3150 ± 25 |
| Load, BHP | 6.5a |
| Fuel Flow, Lb/Hr. | 4.75 ± 0.25 |
| Air/Fuel Ratio | 14.0 ± 0.5 |
| Jacket Outlet Coolant Temp., °F. | 200 ± 2 |
| Gallery Oil Temp., °F. | 290 ± 2 |

TABLE 3

TORQUE ON JOURNAL (LBS. - IN.)

| | | | | | | |
|---|---|---|---|---|---|---|
| | | XVI | XVII | | XIX | XX |
| | | 450 Neutral | 450 Neutral | | SAE 30 Motor | SAE 30 Motor |
| | XV | Oil with 1 wt. % | Oil with 2 wt. % | XVIII | Oil with 1 wt. % | Oil with 2 wt. % |
| True Load | 450 Neutral | Additive of | Additive of | SAE 30 | Additive of | Additive of |
| Lbs. | Oil | Ex. I | Ex. I | Motor Oil | Ex. I | Ex. I |
| 300 | 8 | 7 | 6 | 12 | 7 | 8 |
| 500 | 14 | 10 | 10 | 17 | 12 | 11 |
| 600 | xxx (1) | — | — | — | — | — |
| 750 | | 18 | 17 | 30 | 16 | 15 |
| 800 | | — | — | xxx | — | — |
| 1,000 | | xxx | 20 | | 25 | 20 |
| 1,100 | | | xxx | | — | — |
| 1,250 | | | | | xxx | 26 |
| 1,500 | | | | | | xxx |

(1) xxx indicates failure occurred with the journal scoring and the shear pin breaking.

| Operating Conditions | |
|---|---|
| Spark Advance, BTDC | 35 ± 1 |
| Oil Pressure, PSI | 40 ± 2 |
| Crankcase Vacuum in. H₂O | 2 ± 0.5 |
| Exhaust Back Pressure, in. Hg. | 0.5 ± 0.5 |
| Crankcase Off-Gas, CFH | 30 ± 1 |
| Oil Charge, Pints | 3.5 |

The test is conducted by charging 3.5 pints of the test lubricant to the engine sump. Test duration consists of 40 hours operation at the prescribed test conditions of Table 2 above. When the prescribed gallery oil temperature is reached, the test time begins. Interim oil adjustments are made at the end of 10, 20 and 30 hours of test operation. A copper/lead bearing weight loss of about 40 mg or lower is considered acceptable.

TABLE 2

| Example | Compound of Example I (Wt. %) | Copper Corrosion Inhibitor (B) (Wt. %) | Terephthalic Acid (Wt. %) | Anti-Oxidant (C) (Wt. %) | Amoco (D) PCO-059 | CRC Engine Test 40 hours (BWL, mg) (E) |
|---|---|---|---|---|---|---|
| XIV | ~2 | 0.075 | Present | 0.050 | 7.050 | 30.1 |

(A) 1-hydroxy-3,7-di(methyl phenoxylmethyl)-5-coco-5-aza-1-bora-2,8-dioxacyclooctane
(B) Copper Corrosion Inhibtior = A mixture of 83 weight percent 1,3,4-thiodiazole-2,5-bis(octyldisulfide) and 17 weight percent of 2 mercapto-5 octyldithio-1,3,4-thiadiazole, marketed by the Amoco Oil Company under the Trademark of Amoco 150.
(C) Anti-oxidant = thiodiethyl bis(3,5-di-t-butyl-4-hydroxy) hydrocinnamate.
(D) Amoco PCO-059 = detergent/dispersant package marketed commercially by the Amoco Oil Company.
(E) BWL = bearing weight loss.

EXAMPLES XV TO XX

The compound 1-hydroxy-3,7-di(methyl phenoxy methyl)-5-coco-5-aza-1-bora-2,8-dioxacyclooctane produced in accordance with the procedure of Example I is tested for extreme pressure, anti-wear and friction reducing properties admixed with separate portions of 450 neutral oil and SAE 30 motor at concentrations of 1 and 2 weight percent respectively. Samples of 450 neutral oil and SAE 30 motor oil without the compound 1-hydroxy-3,7-di(methyl phenoxy methyl)-5-coco-5-aza-1-bora-2,8-dioxacyclooctane serve as controls for the experiments.

Each lubricant composition is tested in accordance with the procedure disclosed in ASTM:D3233-73 (reapproved 1978) using a Falex lubricant tester. The test, in accordance with the above ASTM designation, is performed by applying resistance to a revolving metal journal. A rachet mechanism movably attached to two V-blocks applies resistance by steadily increasing pressure on the journal. The metal journal and V-blocks (steel) are submerged in the lubricant composition to be tested. A summary of the results obtained is disclosed in Table 3 below:

As shown in Table 3, the addition of 1-hydroxy-3,7-di(methyl phenoxy methyl)5-coco-5-aza-1-bora-2,8-dioxacyclooctane to 450 neutral oil and SAE 30 motor oil at concentrations of one and two weight percent respectively, imparts extreme pressure properties to the oils.

Obviously, many modifications and variations of the invention, as hereinbefore set forth, may be made without departing from the spirit and scope thereof, and therefore only such limitations should be imposed as are indicated in the appended claims.

We claim:

1. A compound having the formula:

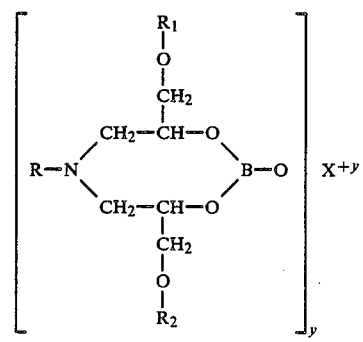

where R is hydrogen or an organic radical having from 1 to about 30 carbon atoms, $R_1$ and $R_2$ are the same or different organic radicals having from 1 to about 50 carbon atoms, y is an integer between 1 and 4 and X is hydrogen or a metal selected from a transition metal having an atomic number of 21 through 30 or a Group IVA metal.

2. The compound defined in claim 1 where R, $R_1$, and $R_2$ are organic radicals which contain at least 75 percent carbon and hydrogen atoms.

3. A compound having the formula:

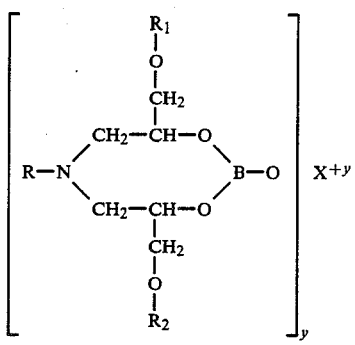

where R is hydrogen or an alkyl, alkene, alkadiene, aryl, akylaryl or arylalkyl radical having from 1 to about 30 carbon atoms, $R_1$ and $R_2$ are the same or different radicals selected from alkyl, aryl, alkylaryl or arylalkyl radicals having from 1 to about 50 carbon atoms, y is an integer between 1 and 4, and x is hydrogen or a metal selected from a transition metal having an atomic number of 21 through 30 or a Group IVA metal.

4. The compound defined in claim 3 where R is hydrogen or an alkyl, alkene, alkadiene, aryl, alkylaryl or arylalkyl radical having from 1 to about 24 carbon atoms.

5. The compound defined in claim 3 where $R_1$ and $R_2$ are the same or different radicals selected from alkyl, aryl, alkylaryl or arylalkyl radicals having from 1 to about 30 carbon atoms.

6. The compound defined in claim 3 where x is a metal selected from the group consisting of scandium, titanium, vanadium, chromium, maganese, iron, cobalt, nickel, copper, zinc, tin and lead and mixtures thereof.

7. A process for producing a bis(hydrocarbyloxy methylated) boron-containing, heterocyclic compound which comprises the steps of:
(A) reacting a primary amine or ammonia in about a 1:2 molar ratio with a glycidyl ether of the formula:

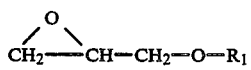

where $R_1$ is alkyl, aryl, alkylaryl or arylalkyl having from 1 to about 50 carbon atoms to produce a reaction product; and
(B) reacting the reaction product of step (A) in about a 1:1 molar ratio with boric acid to produce said bis(hydrocarbyloxy methylated) boron-containing, heterocyclic compound.

8. The process defined in claim 7 where the primary amine is a member selected from the group consisting of methylamine, ethylamine, propylamine, butylamine, octadecylamine, cyclohexylamine, dodecylamine, phenylamine, oleylamine, cocoamine and tallowamine and mixtures thereof.

9. The process defined in claim 7 where the glycidyl ether is a member selected from the group consisting of methyl glycidyl ether, ethyl glycidyl ether, propyl glycidyl ether, butyl glycidyl ether, phenyl glycidyl ether, cresyl glycidyl ether, phenyl methyl glycidyl ether, ethyl phenyl glycidyl ether and phenyl ethyl glycidyl ether and mixtures thereof.

10. The process defined in claim 7, including contacting the bis(hydrocarbyloxy methylated) boron-containing, heterocyclic compound with a metal selected from either a transistion metal having an atomic number of 21 through 30 or a Group IVA metal or a mixture thereof.

11. The process defined in claim 10 where the transition metal or Group IVA metal is a member selected from the group consisting of scandium, titanium, vanadium, chromium, manganese, iron, cobalt, nickel, copper, zinc, tin and lead and mixtures thereof.

12. A compound comprising the reaction product which forms by reacting boric acid, in about a 1:1 molar ratio, with the intermediate reaction product which forms by reacting a primary amine or ammonia in about a 1:2 molar ratio with a glycidyl ether of the formula:

where $R_1$ is alkyl, aryl, alkylaryl or arylalkyl having from 1 to about 50 carbon atoms.

13. The compound defined in claim 12 where said glycidyl ether is reacted with a primary amine selected from the group consisting of methylamine, ethylamine, propylamine, butylamine, octadecylamine, cyclohexylamine, phenylamine, dodecylamine, oleylamine, hexadecylamine, cocoamine and tallowamine and mixtures thereof.

14. The compound defined in claim 12 where said glycidyl ether is reacted with a primary amine having from 1 to about 24 carbon atoms.

15. The compound defined in claim 12 where the glycidyl ether is a member selected from the group consisting of methyl glycidyl ether, ethyl glycidyl ether, propyl glycidyl ether, butyl glycidyl ether, phenyl glycidyl ether, cresyl glycidyl ether, phenyl methyl glycidyl ether, ethyl phenyl glycidyl ether and phenyl ethyl glycidyl ether and mixtures thereof.

16. A lubricating composition comprising a major amount of a lubricating oil and a minor amount of a compound having the formula:

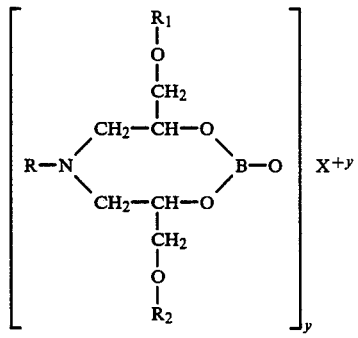

where R is hydrogen or an organic radical having from 1 to about 30 carbon atoms, $R_1$ and $R_2$ are the same or different organic radicals having from 1 to about 50 carbon atoms, y is an integer between 1 and 4 and X is hydrogen or a metal selected from a transition metal having an atomic number of 21 through 30 or a Group IVA metal.

17. The compound defined in claim 16 where R, $R_1$, and $R_2$ are organic radicals which contain at least 75 percent carbon and hydrogen atoms.

18. A lubricating composition comprising a major amount of a lubricating oil and a minor amount of a composition having the formula:

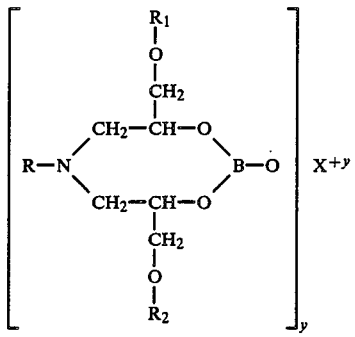

where R is hydrogen or an alkyl, alkene, alkadiene, aryl, alkylaryl or arylalkyl radical having from 1 to about 30 carbon atoms, $R_1$ and $R_2$ are the same or different radical selected from alkyl, aryl, alkylaryl or arylalkyl radicals having from 1 to about 50 carbon atoms, y is an integer between 1 and 4, and x is hydrogen or a metal selected from a transition metal having an atomic number of 21 through 30 or a Group IVA metal.

19. The compound defined in claim 18 where R is hydrogen or an alkyl, alkene, alkadiene, aryl, alkylaryl or arylalkyl radical having from 1 to about 24 carbon atoms.

20. The compound defined in claim 18 where $R_1$ and $R_2$ are the same or different radicals selected from alkyl, aryl, alkylaryl or arylalkyl radicals having from 1 to about 30 carbon atoms.

21. The compound defined in claim 18 where x is a metal selected from the group consisting of scandium, titanium, vanadium, chromium, maganese, iron, cobalt, nickel, copper, zinc, tin and lead and mixtures thereof.

22. A lubricating composition comprising a major amount of a lubricating oil and a minor amount of:
(A) an extreme pressure, anti-wear and friction reducing additive of the formula:

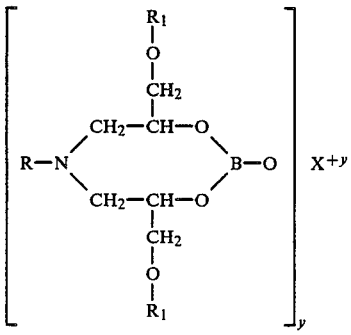

where R is hydrogen or an alkyl, alkene, alkadiene, aryl, alkylaryl or arylalkyl radical having from 1 to about 30 carbon atoms, $R_1$ and $R_2$ are the same or different radicals selected from alkyl, aryl, alkylaryl or arylalkyl radicals having from 1 to about 50 carbon atoms, y is an integer between 1 and 4, and x is hydrogen or a metal selected from a transition metal having an atomic number of 21 through 30 or a Group IVA metal;

(B) A copper corrosion inhibitor comprising a compound having the formula:

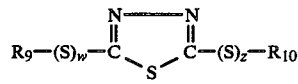

wherein $R_9$ and $R_{10}$ are the same or different moieties selected from hydrogen or straight or branched chain alkyl, cyclic or alicyclic alkyl, aryl, alkylaryl or arylalkyl radicals having from 2 to about 30 carbon atoms, provided that $R_9$ and $R_{10}$ are not both hydrogen and w and z are the same or different integers between 1 and 8;

(C) A lead corrosion inhibitor comprising terephthalic acid; and (D) An oxidation inhibitor selected from the group consisting of:
(i) a metal additive having the formula:

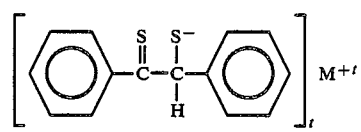

wherein M is a first row transition metal and t is an integer between 1 and 4; and (ii) sulfur bridged, bis hindered phenols having the formula:

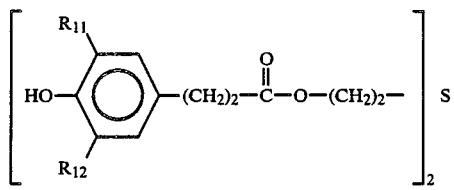

where $R_{11}$ and $R_{12}$ are the same or different alkyl groups having from 1 to 6 carbon atoms.

23. The lubricating composition defined in claim 22 where the extreme pressure, anti-wear and friction reducing additive is a member selected from the group consisting of 1-hydroxy-3,7-di(methoxy methyl)-5-dodecyl-5-aza-1-bora-2,8-dioxacyclooctane; 1-hydroxy-4,6-di(methoxy methyl)-5-dodecyl-5-aza-1-bora-2,8-dioxacyclooctane; 1-hydroxy-3,7-di(ethoxy methyl)-5-dodecyl-5-aza-1-bora-2,8-dioxacyclooctane; 1-hydroxy-3,7-di(propoxy methyl)-5-dodecyl-5-aza-1-bora-2,8-dioxacyclooctane; 1-hydroxy-4,6-di(butoxy methyl)-5-dodecyl-5-aza-1-bora-2,8-dioxacyclooctane; 1-hydroxy-3,7-di(methyl phenoxy methyl)-5-dodecyl-5-aza-1-bora-2,8-dioxacyclooctane; 1-hydroxy-4,6-di(methyl phenoxy methyl)-5-dodecyl-5-aza-1-bora-2,8-dioxacyclooctane; 1-hydroxy-3,7-di(ethyl phenoxy methyl)-5-dodecyl-5-aza-1-bora-2,8-dioxacyclooctane; 1-hydroxy-4,6-di(phenyl methoxy methyl)-5-dodecyl-5-aza-1-bora-2,8-dioxacyclooctane; 1-hydroxy-3,7-di(phenyl ethoxy methyl)-5-dodecyl-5-aza-1-bora-2,8-dioxacyclooctane; 1-hydroxy-3,7-di(methyl phenoxy methyl)-5-coco-5-aza-1-bora-2,8-dioxacyclooctane; 1-hydroxy-3,7-di(methyl phenoxy methyl)-5-tallow-5-aza-1-bora-2,8-dioxacyclooctane and 1-hydroxy-3,7-di(methyl phenoxy methyl)-5-oleyl-5-aza-1-bora-2,8-dioxacyclooctane and mixtures thereof.

24. The lubricating composition defined in claim 22 where x is a metal selected from the group consisting of scandium, titanium, vanadium, chromium, manganese, iron, cobalt, nickel, copper, zinc, tin and lead and mixtures thereof.

25. The lubricating composition defined in claim 22 wherein the extreme pressure, anti-wear and friction reducing additive (A) comprises from 0.1 to about 15 weight percent of said composition.

26. The lubricating composition defined in claim 22 wherein the copper corrosion inhibitor (B) is a member selected from the group consisting of 1,3,4-thiadiazole-2,5-bis(octyldisulfide); 1,3,4-thiadiazole-2,5 bis(octyltrisulfide); 1,3,4-thiadiazole-2,5 bis (octyltetrasulfide); 1,3,4-thiadiazole-2,5 bis (dodecyldisulfide); 1,3,4-thiadiazole-2,5 bis (dodecyltrisulfide); 1,3,4-thiadiazole-2,5 bis (dodecyltetrasulfide); 2lauryldithia-5-thiaalpha-methylstyryl-1,3,4 thiadiazole; 2-lauryltrithia-5-thiaalpha-methylstyryl-1,3,4 thiadiazole; 2 mercapto-5 octyldithio-1,3,4-thiadiazole and 2 mercapto-5 dodecyldithio-1,3,4-thiadiazole and mixtures thereof.

27. The lubricating composition defined in claim 22 where the copper corrosion inhibitor (B) comprises from 0.001 to about 5 weight percent of said composition.

28. The lubricating composition defined in claim 22 where the terephthalic acid comprises from 0.001 to about 1 weight percent of said composition.

29. The lubricating composition defined in claim 22 where the oxidation inhibitor (D) is a metal derivative of bis(dithiobenzil) selected from the group consisting of bis(dithiobenzil) iron, bis(dithiobenzil) cobalt, bis(dithiobenzil) nickel, bis(dithiobenzil) copper, bis (dithiobenzil) zinc, bis(dithiobenzil) vanadium, bis (dithiobenzil) chromium and bis(dithiobenzil) manganese and mixtures thereof.

30. The lubricating composition defined in claim 22 wherein the oxidation inhibitor (D) is a sulfur bridged, bis hindered phenol selected from the group consisting of thiodiethyl bis-(3,5-dimethyl-4-hydroxy) hydrocinnamate; thiodiethyl bis-(3,5-diethyl-4-hydroxy) hydrocinnamate; thiodiethyl bis-(3,5-dipropyl-4-hydroxy) hydrocinnamate; thiodiethyl bis-(3,5-dipentyl-4-hydroxy) hydrocinnamate and thiodiethyl bis-(3,5-dihexyl-4-hydroxy) hydrocinnamate and mixtures thereof.

31. The lubricating composition defined in claim 22 wherein the oxidation inhibitor (D) comprises from 0.01 to about 1 weight percent of said composition.

32. A lubricating composition comprising a major amount of a lubricating oil and a minor amount of:
(A) the reaction product which forms by reacting boric acid, in about a 1:1 molar ratio, with the intermediate reaction product which forms by reacting a primary amine or ammonia in about a 1:2 molar ratio with a glycidyl ether of the formula:

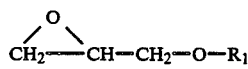

where $R_1$ is alkyl, aryl, alkylaryl or arylalkyl having from 1 to about 30 carbon atoms;
(B) a copper corrosion inhibitor comprising a compound having the formula:

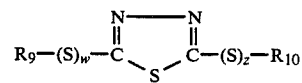

wherein $R_9$ and $R_{10}$ are moieties selected from hydrogen or straight or branched chain alkyl, cyclic or alicyclic alkyl, aryl, alkylaryl or arylalkyl radicals having from 2 to about 30 carbon atoms, provided that $R_9$ and $R_{10}$ are not both hydrogen and w and z are the same or different integers between 1 and 8;
(C) a lead corrosion inhibitor comprising terephthalic acid; and
(D) An oxidation inhibitor selected from the group consisting of:
(i) a metal additive having the formula:

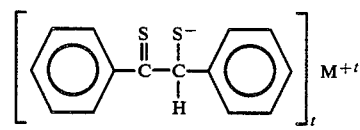

where M is a first row transition metal and t is an integer between 1 and 4; and
(ii) sulfur bridged, bis hindered phenols having the formula:

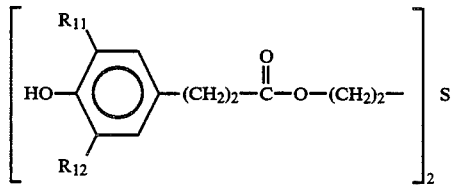

where $R_{11}$ and $R_{12}$ are the same or different alkyl groups having from 1 to 6 carbon atoms.

33. The lubricating composition defined in claim 32 wherein the oxidation inhibitor (D) comprises a sulfur bridged, bis hindered phenol of formula:

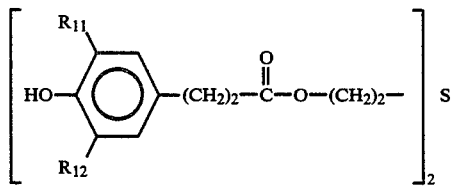

where $R_{11}$ and $R_{12}$ are the same or different alkyl groups having from 1 to 6 carbon atoms.

34. The lubricating composition defined in claim 22 wherein the oxidation inhibitor (D) comprises a sulfur bridged, bis hindered phenol of formula:

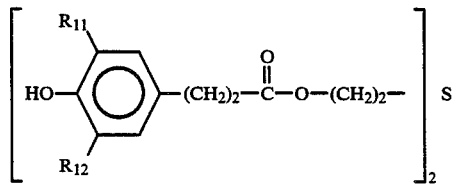

where $R_{11}$ and $R_{12}$ are the same or different alkyl groups having from 1 to 6 carbon atoms.

* * * * *